United States Patent
Tanabe

(10) Patent No.: US 11,162,926 B2
(45) Date of Patent: Nov. 2, 2021

(54) CHEMILUMINESCENCE TYPE NITROGEN OXIDE CONCENTRATION METER

(71) Applicant: SHIMADZU CORPORATION, Kyoto (JP)

(72) Inventor: Ryo Tanabe, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 272 days.

(21) Appl. No.: 16/404,920

(22) Filed: May 7, 2019

(65) Prior Publication Data
US 2020/0355663 A1 Nov. 12, 2020

(51) Int. Cl.
- *G01N 21/76* (2006.01)
- *G01N 21/01* (2006.01)
- *G01N 33/00* (2006.01)

(52) U.S. Cl.
CPC ....... *G01N 33/0037* (2013.01); *G01N 21/766* (2013.01); *G01N 2021/0193* (2013.01)

(58) Field of Classification Search
CPC . Y10T 436/177692; Y10T 436/178459; Y10T 436/179228; G01N 21/766; G01N 33/0037; B01D 53/261; B01D 53/263
See application file for complete search history.

(56) References Cited

U.S. PATENT DOCUMENTS

2017/0176378 A1* 6/2017 Otjes ................. G01N 33/0037

FOREIGN PATENT DOCUMENTS

| JP | H05-196574 A | * | 8/1993 |
| JP | 2001-153857 A | * | 6/2001 |
| JP | 2002-148192 A | | 5/2002 |
| JP | 2018-072032 A | | 5/2018 |

* cited by examiner

*Primary Examiner* — Christopher Adam Hixson
*Assistant Examiner* — Michelle Adams
(74) *Attorney, Agent, or Firm* — Sughrue Mion, PLLC

(57) ABSTRACT

In a chemiluminescence type nitrogen oxide concentration meter, a mixed gas of air with its moisture adsorbed by an adsorption apparatus and air that through a fifth flow path without the adsorption apparatus in between is flown into an ozone generator. Therefore, ozone can be generated using air of proper humidity in the ozone generator 7. As a result, ozone can be efficiently generated while suppressing occurrence of metal contamination in the ozone generator 7. Then, in the reaction unit 8, nitrogen oxides in the sample gas are made to appropriately show chemiluminescence using the ozone, and in the detector 9, the intensity of light generated in the reaction unit 8 is detected. Furthermore, in the control unit 10, the concentration of nitrogen oxides in the sample gas is measured, based on the intensity of light detected by the detector 9.

4 Claims, 2 Drawing Sheets

CHEMILUMINESCENCE TYPE NITROGEN OXIDE CONCENTRATION METER

CROSS REFERENCE TO RELATED APPLICATIONS

This application relates to, but does not claim priority from, JP Ser. No.: JP2016-208830 filed on Oct. 25, 2016 and published as JP Pub. No.: JP2018-72032 on May 10, 2018, the entire contents of which are incorporated herein fully by reference.

BACKGROUND OF THE INVENTION

Field of the Invention

The present invention relates to a chemiluminescence type nitrogen oxide concentration meter including an ozone generator for generating ozone.

Description of the Related Art

Conventionally, a chemiluminescence type nitrogen oxide concentration meter is utilized as a device for measuring the concentration of nitrogen oxides contained in a sample gas.

The chemiluminescence type nitrogen oxide concentration meter includes an ozone generator, a reaction tank, a detector, and the like. In the chemiluminescence type nitrogen oxide concentration meter, the sample gas is supplied to the reaction tank, and ozone generated in the ozone generator is supplied to the reaction tank. Then, in the reaction tank, the sample gas and ozone are chemically reacted to generate light. At this time, the detector detects the intensity of the light generated in the reaction tank. Then, based on the detection result of the detector, the concentration of nitrogen oxides in the sample gas is measured (see, for example, JP-A-2002-148192).

The ozone generator used in such chemiluminescence type nitrogen oxide concentration meter includes, for example, an electrode, a dielectric provided so as to cover the electrode, a conductor, and the like. When a voltage is applied to the electrode, silent discharge occurs between the dielectric and the conductor, and a part of oxygen in the atmosphere becomes ozone. The ozone generated in this way is supplied to the reaction tank.

SUMMARY OF THE INVENTION

Problems to be Solved by the Invention

In a conventional chemiluminescence type nitrogen oxide concentration meter, the accuracy of measuring the concentration of nitrogen oxides sometimes lowered. Specifically, an ozone generator can generate a large amount of ozone as the humidity of flown air is lower. Therefore, the conventional chemiluminescence type nitrogen oxide concentration meter flows air with low humidity into the ozone generator, for example, by providing an apparatus for dehumidifying air on the upstream side of the ozone generator in the moving direction of the air.

However, in a case where the humidity of the air flowing into the ozone generator is too low, metal contamination (impurities) occurs from the surface of a conductor when performing silent discharge in the ozone generator. Moreover, when metal contamination occurs, transmission of light generated in a reaction tank to a detector is hindered, and the detection accuracy of the detector is lowered. As a result, the accuracy of measuring the concentration of nitrogen oxides is lowered.

In the ozone generator, the fact that occurrence of metal contamination is suppressed when the humidity of the air is high, and a large amount of metal contamination is caused when the humidity of the air is low is assumed to result from the fact that the surface of the conductor is protected by moisture in the air.

The present invention has been made in view of the above circumstances, and it is an object of the present invention to provide a chemiluminescence type nitrogen oxide concentration meter capable of accurately measuring the concentration of nitrogen oxides in a sample gas while efficiently generating ozone in the ozone generator.

Means for Solving the Problems (1) A chemiluminescence type nitrogen oxide concentration meter according to the present invention includes a dehumidifier, an adsorption apparatus, an introduction flow path, a lead-out flow path, a bypass flow path, an ozone generator, a reaction unit, a detector, and a measurement unit. The dehumidifier dehumidifies air by cooling the air. The adsorption apparatus adsorbs moisture in the air dehumidified by the dehumidifier. The introduction flow path introduces the air dehumidified by the dehumidifier from the dehumidifier into the adsorption apparatus. The lead-out flow path leads out the air with its moisture adsorbed by the adsorption apparatus. The bypass flow path connects the introduction flow path and the lead-out flow path without the adsorption apparatus in between. The ozone generator generates ozone using a mixed gas of a first air through the adsorption apparatus and a second air through the bypass flow path. The reaction unit causes chemiluminescence of nitrogen oxides in a sample gas using ozone generated in the ozone generator. The detector detects an intensity of light generated by chemiluminescence in the reaction unit. The measurement unit measures a concentration of nitrogen oxides in the sample gas, based on the intensity of light detected by the detector.

With such a configuration, a mixed gas of air dehumidified by the dehumidifier, with its moisture adsorbed by the adsorption apparatus, and air dehumidified by the dehumidifier, which through the bypass flow path without the adsorption apparatus in between flows into the ozone generator. That is, the mixed gas of two types of air with different humidity flows into the ozone generator. Then, ozone is generated using the mixed gas of two types of air with different humidity in the ozone generator.

Therefore, ozone can be generated using air of proper humidity in the ozone generator.

As a result, ozone can be efficiently generated while suppressing occurrence of metal contamination in the ozone generator.

Then, nitrogen oxides in the sample gas are made to appropriately show chemiluminescence using the ozone in a reaction unit, and the intensity of light generated in the reaction unit is detected in a detector. Furthermore, the concentration of nitrogen oxides in the sample gas is measured in the measurement unit, based on the intensity of light detected by the detector.

Therefore, the light generated in the reaction unit can be accurately detected in the detector, and the concentration of the nitrogen oxide in the sample gas can be accurately measured in the measurement unit.

As described above, according to the chemiluminescence type nitrogen oxide concentration meter of the present invention, the concentration of nitrogen oxides in the sample gas can be accurately measured while efficiently generating ozone in the ozone generator.

(2) Further, the moisture concentration in the mixed gas may range from 100 to 1000 ppm.

With such a configuration, air with a proper moisture concentration can be supplied to the ozone generator. Then, ozone can be efficiently generated using the air in the ozone generator.

(3) Also, a difference between flow path resistances of the introduction flow path and the bypass flow path may cause a difference in a flow rate between the first air passing through the adsorption apparatus and the second air passing through the bypass flow path.

With such a configuration, the air with a proper moisture concentration can be supplied to the ozone generator with a simple configuration.

(4) Moreover, a flow rate ratio of the flow rate of the air passing through the adsorption apparatus and the flow rate of the air passing through the bypass flow path without interposing the adsorption apparatus may range from 10:1 to 100:1.

With such a configuration, the air with a proper moisture concentration can be supplied to the ozone generator, by appropriately maintaining the flow rate ratio of the flow rate of the air passing through the adsorption apparatus and the flow rate of the air passing through the bypass flow path without interposing the adsorption apparatus.

Effects of Invention

According to the present invention, a mixed gas of air dehumidified by the dehumidifier, from which the moisture has been adsorbed by the adsorption apparatus, and air dehumidified by the dehumidifier, which has passed through the bypass flow path without interposing the adsorption apparatus flows into the ozone generator. Therefore, ozone can be generated using air of proper humidity in the ozone generator. As a result, ozone can be efficiently generated while suppressing occurrence of metal contamination in the ozone generator. Then, nitrogen oxides in the sample gas are made to appropriately show chemiluminescence using the ozone in a reaction unit, and the intensity of light generated in the reaction unit is detected in a detector. Furthermore, the concentration of nitrogen oxides in the sample gas is measured in the measurement unit, based on the intensity of light detected by the detector. Therefore, the light generated in the reaction unit can be accurately detected in the detector, and the concentration of the nitrogen oxide in the sample gas can be accurately measured in the measurement unit.

MODE FOR CARRYING OUT THE INVENTION

Figure 1:
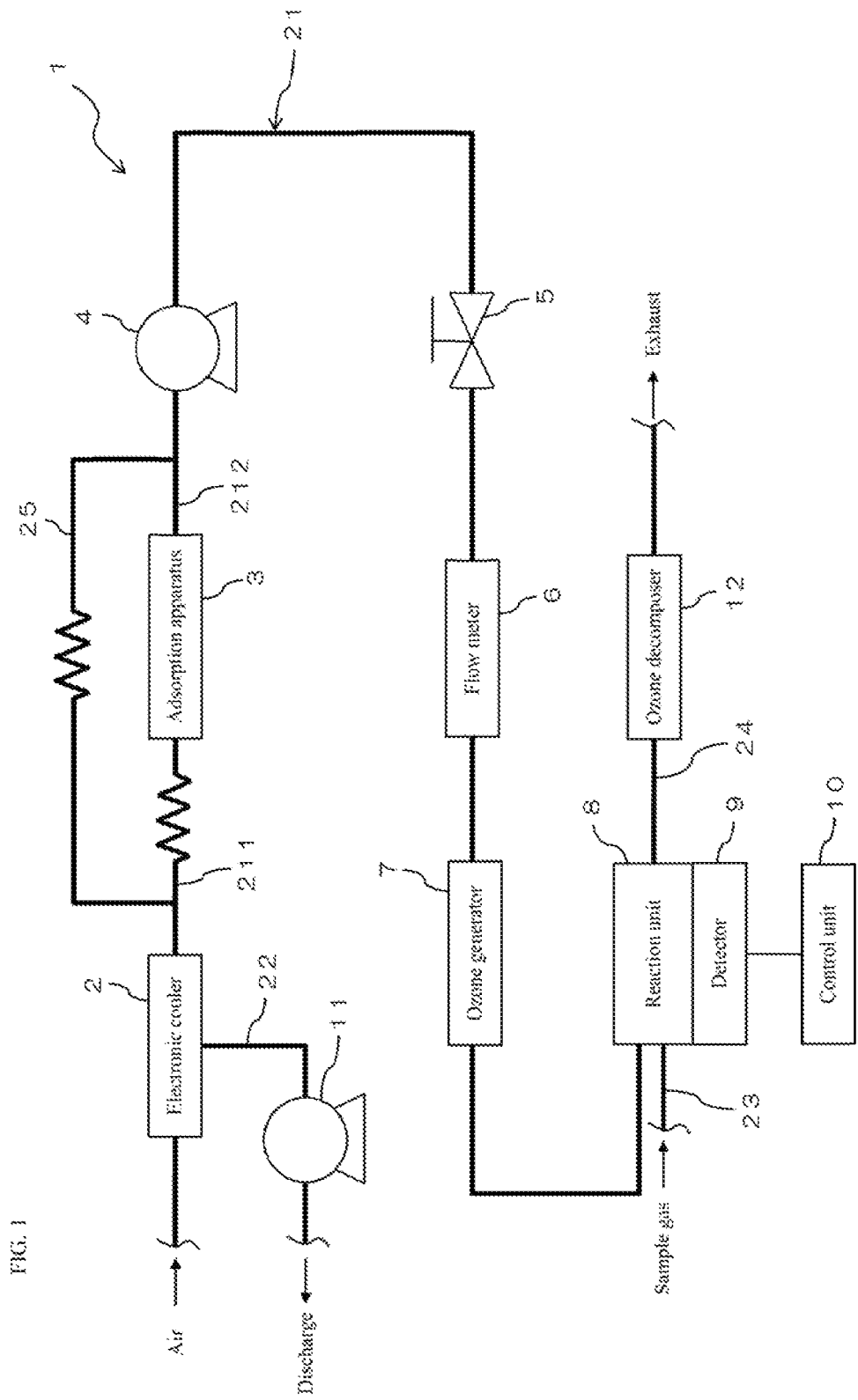
FIG. 1 is a schematic diagram showing a configuration of a chemiluminescence type nitrogen oxide concentration meter according to one embodiment of the present invention.

1. Overall Configuration of Chemiluminescence Type Nitrogen Oxide Concentration Meter FIG. 1 is a schematic diagram showing a configuration of a chemiluminescence type nitrogen oxide concentration meter 1 according to one embodiment of the present invention.

The chemiluminescence type nitrogen oxide concentration meter 1 is a device for measuring the concentration of nitrogen oxides contained in a sample gas. The chemiluminescence type nitrogen oxide concentration meter 1 includes an electronic cooler 2, an adsorption apparatus 3, a first pump 4, a valve 5, a flow meter 6, an ozone generator 7, a reaction unit 8, a detector 9, a control unit 10, a second pump 11, and an ozone decomposer 12. Further, in the chemiluminescence type nitrogen oxide concentration meter 1, a first flow path 21, a second flow path 22, a third flow path 23, a fourth flow path 24, and a fifth flow path 25 are formed.

The first flow path 21 is a flow path for taking in air and mixing ozone ($O_3$) into the air and flowing it into the reaction unit 8. In the first flow path 21, the electronic cooler 2, the adsorption apparatus 3, the first pump 4, the valve 5, the flow meter 6 and the ozone generator 7 are interposed in this order, and an end on a downstream side in the moving direction of the air is connected to the reaction unit 8.

The electronic cooler 2 is for adjusting the air flown into the first flow path 21 so that its temperature and humidity become respectively constant. Specifically, the electronic cooler 2 dehumidifies by cooling the air flown into the first flow path 21. The electronic cooler 2 is an example of a dehumidifier. To the electronic cooler 2, one end of the second flow path 22 is connected. In the second flow path 22, a second pump 11 is interposed. By operating the second pump 11, moisture removed from the air in the electronic cooler 2 is discharged via the second flow path 22.

The adsorption apparatus 3 is an apparatus that adsorbs moisture contained in the air dehumidified by the electronic cooler 2. Specifically, the adsorption apparatus 3 stores an adsorbent therein, and moisture contained in the air is adsorbed and removed by the adsorbent, thereby performing dehumidification. The adsorbent is, for example, silica gel, and is composed of a plurality of particles. However, the adsorbent may be particles made of other materials such as molecular sieves.

The first pump 4 sucks air into the first flow path 21, causes the sucked air to pass through the first flow path 21, and sends the air to the reaction unit 8.

The valve 5 is for adjusting the flow rate of the air moving in the first flow path 21 to be constant. The valve 5 is, for example, a needle valve.

The flow meter 6 is for measuring the flow rate of the air moving in the first flow path 21.

The ozone generator 7 is an apparatus for generating ozone using the air moving in the first flow path 21. Specifically, the ozone generator 7 generates ozone by silent discharge or the like.

One end of the third flow path 23 is connected to the reaction unit 8. Air containing ozone is flown into the reaction unit 8 via the first flow path 21, and the sample gas is supplied to the reaction unit 8 via the third flow path 23. The reaction unit 8 causes chemiluminescence of nitrogen oxides contained in the sample gas, using ozone contained in the air.

The detector 9 is adjacent to the reaction unit 8. The detector 9 includes, for example, a glass window or the like, and is configured so that light generated by chemiluminescence in the reaction unit 8 can be taken in. The detector 9 is configured to detect the intensity of light generated in the reaction unit 8.

The control unit 10 includes, for example, a Central Processing Unit (CPU). The control unit 10 is electrically connected to the detector 9. The control unit 10 controls the operation of the detector 9 and measures the concentration of nitrogen oxides in the sample gas, based on the intensity of light detected by the detector 9. The control unit 10 is an example of the measurement unit.

One end of the fourth flow path 24 is connected to the reaction unit 8. In the fourth flow path 24, an ozone decomposer 12 is interposed.

The ozone decomposer 12 decomposes unreacted ozone contained in the air by thermal decomposition or the like.

As will be described in detail later, a fifth flow path 25 is connected to the first flow path 21. In the moving direction of the air, one end of the fifth flow path 25 is connected to a portion on the upstream side of the adsorption apparatus 3 in the first flow path 21, and the other end of the fifth flow path 25 is connected to a portion on the downstream side of the adsorption apparatus 3 in the first flow path 21. The fifth flow path 25 is an example of a bypass flow path.

In the chemiluminescence type nitrogen oxide concentration meter 1, the first pump 4 and the second pump 11 are operated, and the opening of the valve 5 is adjusted so that the flow rate detected by the flow meter 6 becomes constant. Then, a certain amount of air is sucked into the first flow path 21 and moves in the first flow path 21.

At this time, the air moving in the first flow path 21 is cooled and dehumidified by the electronic cooler 2. The moisture removed from the air in the electronic cooler 2 is discharged from the second flow path 22.

The air dehumidified by the electronic cooler 2 is divided into air moving in the first flow path 21 as it is and air flowing from the first flow path 21 into the fifth flow path 25. That is, the air dehumidified by the electronic cooler 2 moves in the first flow path 21 as it is and is introduced into the adsorption apparatus 3, and a part thereof flows into the fifth flow path 25 and joins the first flow path 21 without interposing the adsorption apparatus 3. The mixed air flows into the ozone generator 7. Then, ozone is generated using this mixed gas in the ozone generator 7. Ozone generated in the ozone generator 7 flows into the reaction unit 8 together with the air. Further, a sample gas is supplied to the reaction unit 8 via the third flow path 23.

Then, in the reaction unit 8, the sample gas and ozone are chemically reacted to generate light. At this time, the detector 9 detects the intensity of the light generated in the reaction unit 8. The control unit 10 measures the concentration of nitrogen oxides in the sample gas, based on the detection result of the detector 9. Further, in air that has passed through the reaction unit 8, unreacted ozone is decomposed by the ozone decomposer 12 in the process of moving the fourth flow path 24, and then the air is exhausted.

2. Detailed Configuration of Flow Path

As described above, in the chemiluminescence type nitrogen oxide concentration meter 1, most of the air dehumidified by the electronic cooler 2 moves in the first flow path 21 as it is, and a part of the air bypasses by moving in the fifth flow path 25, then joins the first flow path 21.

In the first flow path 21, a portion between the electronic cooler 2 and the adsorption apparatus 3 is formed as an introduction flow path 211, and a portion between the adsorption apparatus 3 and the first pump 4 is formed as a lead-out flow path 212. The introduction flow path 211 is a flow path for introducing the air dehumidified by the electronic cooler 2 from the electronic cooler 2 to the adsorption apparatus 3. The lead-out flow path 212 is a flow path for leading the air from which the moisture has been adsorbed by the adsorption apparatus 3 from the adsorption apparatus 3.

One end of the fifth flow path 25 is connected to the introduction flow path 211, and the other end thereof is connected to the lead-out flow path 212.

Each of the introduction flow path 211 and the fifth flow path 25 has a flow path resistance corresponding to the inner diameter and the length (dimension) thereof. The introduction flow path 211 and the fifth flow path 25 are formed so that their flow path resistances are different from each other. Specifically, the flow path resistance of the introduction flow path 211 is smaller than the flow path resistance of the fifth flow path 25.

3. Detailed Configuration of Ozone Generator

Figure 2:
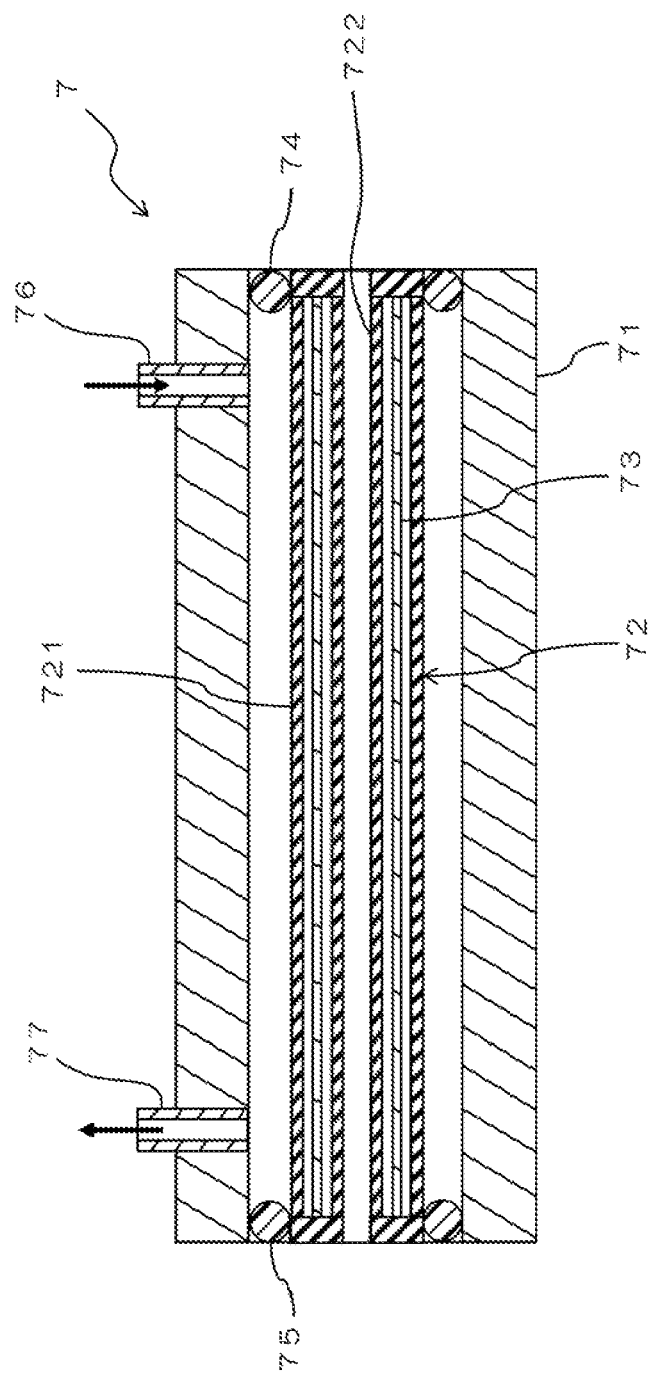
FIG. 2 is a cross-sectional view showing the ozone generator of FIG. 1.

FIG. 2 is a cross-sectional view showing the ozone generator 7.

The ozone generator 7 includes a conductor 71, a dielectric 72, an electrode 73, a first O-ring 74, a second O-ring 75, an inflow pipe 76, and an outflow pipe 77.

The conductor 71 is formed in an elongated cylindrical shape. The conductor 71 is made of, for example, a metal material such as titanium or stainless steel.

The dielectric 72 is disposed in the internal space of the conductor 71. The dielectric 72 is formed in an elongated shape and extends along the axial direction of the conductor 71. The dielectric 72 is made of, for example, a glass material. The dielectric 72 includes an outer cylinder 721 and an inner cylinder 722.

The outer cylinder 721 is formed in an elongated cylindrical shape.

The inner cylinder 722 is disposed in the outer cylinder 721. The outer cylinder 721 and the inner cylinder 722 extend in the axial direction and are arranged at an interval in an orthogonal direction orthogonal to the axial direction. The end edge of the inner cylinder 722 and the end edge of the outer cylinder 721 are covered with a plate-like member.

The electrode 73 is arranged in a space between the outer cylinder 721 and the inner cylinder 722. The electrode 73 is formed in an elongated cylindrical shape and extends along the axial direction. The electrode 73 is made of, for example, aluminum.

The first O-ring 74 is arranged between one end of the conductor 71 and one end of the dielectric 72 to hermetically seal them.

The second O-ring 75 is arranged between the other end of the conductor 71 and the other end of the dielectric 72 to hermetically seal them.

The inflow pipe 76 is formed in a cylindrical shape extending in the orthogonal direction. The inflow pipe 76 is attached to the conductor 71 so as to penetrate the circumferential surface of one end of the conductor 71 in the orthogonal direction. The internal space of the inflow pipe 76 is continuous with the internal space of the conductor 71. One end in the middle of the first flow path 21 is connected to the inflow pipe 76 (see FIG. 1).

The outflow pipe 77 is formed in a cylindrical shape extending in the orthogonal direction. The outflow pipe 77 is attached to the conductor 71 so as to penetrate the circumferential surface of the other end of the conductor 71 in the orthogonal direction. The internal space of the outflow pipe 77 is continuous with the internal space of the conductor 71. The other end in the middle of the first flow path 21 is connected to the outflow pipe 77 (see FIG. 1).

4. Air Flow in Chemiluminescence Type Nitrogen Oxide Concentration Meter

In the chemiluminescence type nitrogen oxide concentration meter 1, a certain amount of air is sucked into the first flow path 21 by operating the first pump 4 shown in FIG. 1, as described above. This air is dehumidified by being cooled by the electronic cooler 2. Specifically, the air sucked into the first flow path 21 becomes air that is saturated at 2° C. with a moisture concentration of about 7000 ppm, by the electronic cooler 2.

Further, as described above, the flow path resistance of the introduction flow path 211 is smaller than the flow path resistance of the fifth flow path 25. As a result, air flows so that the flow rate of the air passing through the electronic cooler 2, then moving in the introduction flow path 211 as it is and passing through the adsorption apparatus 3 and the flow rate of the air passing through the electronic cooler 2 and then passing through the fifth flow path 25 without interposing the adsorption apparatus 3 are different. Specifically, the flow rate of the air passing through the adsorption apparatus 3 is greater than the flow rate of the air passing through the fifth flow path 25 without interposing the adsorption apparatus 3. More specifically, the flow rate ratio of the flow rate of the air passing through the adsorption apparatus 3 and the flow rate of the air passing through the fifth flow path 25 without interposing the adsorption apparatus 3 ranges from 10:1 to 100:1.

The moisture concentration of the air immediately after passing through the adsorption apparatus 3 is about 10 ppm. Then, the air with this moisture concentration moves in the lead-out flow path 212. In addition, the fifth flow path 25 is connected to the lead-out flow path 212, and the air with the above moisture concentration (about 7000 ppm) flows in. As a result, the moisture concentration in the mixed gas of the air that has passed through the adsorption apparatus 3 and the air that has passed through the fifth flow path 25 without interposing the adsorption apparatus 3 ranges from 100 to 1000 ppm. Then, this mixed gas is supplied to the ozone generator 7, and ozone is generated by the ozone generator 7.

Specifically, the mixed gas is flown into a region between the conductor 71 and the dielectric 72 via the inflow pipe 76, and a voltage is applied to the electrode 73, in the ozone generator 7. As a result, silent discharge occurs between the conductor 71 and the dielectric 72, and a part of oxygen in the mixed gas becomes ozone. Then, the ozone is discharged from the ozone generator 7 via the outflow pipe 77 together with the mixed gas, and is supplied to the reaction unit 8 via the first flow path 21.

5. Action Effect (1) In the present embodiment, as shown in FIG. 1, in the chemiluminescence type nitrogen oxide concentration meter 1, a mixed gas of air dehumidified by the electronic cooler 2, with its moisture adsorbed by the adsorption apparatus 3 (a first air), and air dehumidified by the electronic cooler 2, which through the fifth flow path 25 without the adsorption apparatus 3 in between (a second air) flows into the ozone generator 7. That is, the mixed gas of two types of air with different humidity flows into the ozone generator 7. Then, ozone is generated using the mixed gas of the two types of air with different humidity in the ozone generator 7.

Therefore, ozone can be generated using air of proper humidity in the ozone generator 7.

As a result, ozone can be efficiently generated while suppressing occurrence of metal contamination in the ozone generator 7.

Then, in the reaction unit 8, nitrogen oxides in the sample gas are made to appropriately show chemiluminescence using the ozone, and in the detector 9, the intensity of light generated in the reaction unit 8 is detected. Furthermore, in the control unit 10, the concentration of nitrogen oxides in the sample gas is measured, based on the intensity of light detected by the detector 9.

Therefore, the light generated in the reaction unit 8 can be accurately detected in the detector 9, and the concentration of the nitrogen oxide in the sample gas can be accurately measured in the control unit 10.

(2) Also, in the present embodiment, in the chemiluminescence type nitrogen oxide concentration meter 1, the moisture concentration in the mixed gas of the air that has passed through the adsorption apparatus 3 and the air that has passed through the fifth flow path 25 without interposing the adsorption apparatus 3 ranges from 100 to 1000 ppm.

Therefore, air with a proper moisture concentration can be supplied to the ozone generator 7. Then, ozone can be efficiently generated using the air in the ozone generator 7.

(3) Moreover, in the present embodiment, the flow path resistance of the introduction flow path 211 is formed smaller than the flow path resistance of the fifth flow path 25 in the chemiluminescence type nitrogen oxide concentration meter 1. As a result, air flows so that the flow rate of the air passing through the electronic cooler 2, then moving in the introduction flow path 211 as it is and passing through the adsorption apparatus 3 and the flow rate of the air passing through the electronic cooler 2 and then passing through the fifth flow path 25 without interposing the adsorption apparatus 3 are different. Specifically, the flow rate of the air passing through the adsorption apparatus 3 is greater than the flow rate of the air passing through the fifth flow path 25 without interposing the adsorption apparatus 3.

Therefore, air with a proper moisture concentration can be supplied to the ozone generator 7 with a simple configuration.

(4) Further, in the present embodiment, in the chemiluminescence type nitrogen oxide concentration meter 1, the flow rate ratio of the flow rate of the air passing through the adsorption apparatus 3 and the flow rate of the air passing through the fifth flow path 25 without interposing the adsorption apparatus 3 ranges from 10:1 to 100:1.

Therefore, the air with a proper moisture concentration can be supplied to the ozone generator 7, by appropriately maintaining the flow rate ratio of the flow rate of the air passing through the adsorption apparatus 3 and the flow rate of the air passing through the fifth flow path 25 without interposing the adsorption apparatus 3.

6. Modified Examples

In the embodiment described above, it has been described that it is formed so that the flow path resistance of the introduction flow path 211 and the flow path resistance of the fifth flow path 25 are different from each other, whereby the flow rate of the air passing through the adsorption apparatus 3 and the flow rate of the air passing through the fifth flow path 25 without interposing the adsorption apparatus 3 are mixed at a constant ratio. However, it may be formed so that the flow path resistance of the introduction flow path 211 and the flow path resistance of the fifth flow path 25 are the same, and a switching unit for switching the flow path is provided at a branch part between the introduction flow path 211 and the fifth flow path 25, further, a moisture sensor for detecting the moisture content is provided after a joining part of the lead-out flow path 212 and the fifth flow path 25. Then, the switching unit is switched as appropriate based on the detection result of the moisture sensor, whereby the flow rate of the air passing through the adsorption apparatus 3 and the flow rate of the air passing through the fifth flow path 25 without interposing the adsorption apparatus 3 are mixed at a constant ratio.

What is claimed is:

1. A chemiluminescence type nitrogen oxide concentration meter comprising:
   a dehumidifier configured to dehumidify air by cooling the air;
   an adsorption apparatus configured to adsorb moisture in a first portion of the air dehumidified by the dehumidifier;
   an introduction flow path arranged to introduce the first portion of the air dehumidified by the dehumidifier from the dehumidifier into the adsorption apparatus;
   a lead-out flow path arranged to lead out a first air from the adsorption;
   a bypass flow path connecting the introduction flow path and the lead-out flow path without the adsorption apparatus in between;
   an ozone generator configured to generate ozone using a mixed gas of the first air from the adsorption apparatus and a second air from the bypass flow path;
   a reactor configured to cause chemiluminescence of nitrogen oxides in a sample gas using ozone generated in the ozone generator;
   a light detector configured to detect an intensity of light generated by chemiluminescence in the reactor unit; and
   a processor configured to determine a concentration of nitrogen oxides in the sample gas, based on the intensity of light detected by the light detector.

2. The chemiluminescence type nitrogen oxide concentration meter according to claim 1, wherein a moisture concentration in the mixed gas ranges from 100 to 1000 ppm.

3. The chemiluminescence type nitrogen oxide concentration meter according to claim 1, wherein a difference between flow path resistances of the introduction flow path and the bypass flow path causes a difference between a flow rate of the first air from the adsorption apparatus and a flow rate of the second air from the bypass flow path.

4. The chemiluminescence type nitrogen oxide concentration meter according to claim 3, wherein a flow rate ratio of the flow rate of the first air from the adsorption apparatus and the flow rate of the second air from the bypass flow path ranges from 10:1 to 100:1.

* * * * *